(12) United States Patent
Kincade et al.

(10) Patent No.: US 6,177,412 B1
(45) Date of Patent: Jan. 23, 2001

(54) INSECTICIDAL COMPOSITION AND METHOD FOR THE USE THEREOF

(75) Inventors: Robert T. Kincade, Greenville, MS (US); David East, Chilton, WI (US)

(73) Assignee: Valent U.S.A. Corporation, Walnut Creek, CA (US)

( * ) Notice: Under 35 U.S.C. 154(b), the term of this patent shall be extended for 0 days.

(21) Appl. No.: 09/321,737

(22) Filed: May 28, 1999

(51) Int. Cl.[7] .......................... A01N 43/40; A01N 57/00
(52) U.S. Cl. ............................ 514/120; 514/345
(58) Field of Search ................... 514/120, 345

(56) References Cited

U.S. PATENT DOCUMENTS

| | | | |
|---|---|---|---|
| 3,716,600 | 2/1973 | Magee | 260/959 |
| 3,845,172 | 10/1974 | Magee | 260/956 |
| 3,914,417 | 10/1975 | Magee | 424/219 |
| 4,048,235 | 9/1977 | Karrer | 260/612 R |
| 4,218,444 | 8/1980 | Koundakijan | 424/212 |
| 4,562,213 | 12/1985 | Nishida et al. | 514/721 |
| 5,021,412 | 6/1991 | Nakaya et al. | 514/223.8 |
| 5,302,619 | 4/1994 | Shuto et al. | 514/718 |
| 5,369,100 | 11/1994 | Cummings | 514/120 |
| 5,464,613 | 11/1995 | Barcay et al. | 424/84 |
| 5,464,623 | 11/1995 | Chan et al. | 424/405 |
| 5,488,043 | 1/1996 | Yamada et al. | 514/120 |
| 5,530,015 | 6/1996 | Sakamoto et al. | 514/345 |
| 5,698,540 | 12/1997 | Katayama et al. | 514/120 |
| 5,730,996 | 3/1998 | Beall et al. | 424/405 |
| 5,798,346 | 8/1998 | Bloomberg et al. | 514/137 |
| 5,820,855 | 10/1998 | Barcay et al. | 424/84 |

FOREIGN PATENT DOCUMENTS

WO 96/11909   4/1996   (WO) .

OTHER PUBLICATIONS

Delta Agricultural Digest, pp. 1,64, 66–67 (1998).
Martin et al., Effects of Selected Synergists on Inscticide Toxicity in Tobacco Budworm (Lepidoptera: Noctuidae) in Laboratory and Field Studies, Journal Of Economic Entomology, vol. 90, No. 3, pp. 723–731 (1997).
Kanga et al., Tolerance to Cypermethrin and Endosulfan in Field Populations of the Bollworm (Lepidoptera: Noctuidae) from Texas, Journal Of Economic Entomology, vol. 89, No. 3, pp. 583–589 (1996).
Kanga et al., Monitoring for Resistance to Organophosphorus, Carbamate, and Cyclodiene Insecticides in Tobacco Budworm Adults (Lepidoptera: Noctuidae), Journal Of Economic Entomology, vol. 88, No. 5, pp. 1144–1149 (1995).
Elzen et al., Resistance to Pyrethroid, Carbamate, and Organophosphate Insecticides in Field Populations of Tobacco Budworm (Lepidoptera: Noctuidae) in 1990, Journal Of Economic Entomology, vol. 85, No. 6, pp. 2064–2072 (1992).

Primary Examiner—Allen J. Robinson
(74) Attorney, Agent, or Firm—Sughrue, Mion, Zinn, Macpeak & Seas, PLLC

(57) ABSTRACT

An insecticidal composition includes (1) at least one compound of formula (I):

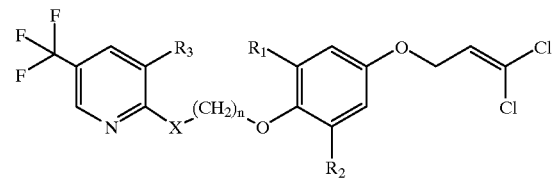

(I)

wherein $R_1$ is bromine, chlorine, methyl, or ethyl, $R_2$ is bromine, chlorine, or ethyl, $R_3$ is hydrogen, halogen, or trifluoromethyl, X is —O—, —S—, or —NH—, and n is 2, 3, or 4, and (2) at least one compound of formula (II):

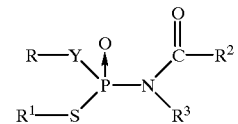

(II)

wherein R and $R^1$ independently are an alkyl, alkenyl, or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms, or an alkynyl group containing 3 to 18 carbon atoms, $R^3$ is hydrogen or an alkyl group containing 1 to 6 carbon atoms, and Y is —O— or —S—. A method for killing insects such as the tobacco budworm and other Lepidopteran pests of cotton includes applying an insecticidally effective amount of such a composition to an area to be treated.

18 Claims, No Drawings

INSECTICIDAL COMPOSITION AND METHOD FOR THE USE THEREOF

FIELD OF THE INVENTION

The present invention is directed to an insecticidal composition and to a method for the use thereof. In particular, the present invention is directed to an insecticidal composition which takes advantage of the synergistic action of two particular insecticides and to a method of using the composition to kill insects such as the tobacco budworm and other Lepidopteran pests of cotton.

BACKGROUND OF THE INVENTION

The tobacco budworm and other Lepidopteran insects are serious pests of cotton fruit (squares and bolls). Moderate or heavy infestations can dramatically reduce lint yields.

The tobacco budworm, *Heliothis virescens*, and cotton bollworm, *Helicoverpa zea*, have developed resistance to major classes of insecticides used to control them, as discussed in Martin et al., "Effects of Selected Synergists on Insecticide Toxicity in Tobacco Budworm (Lepidoptera: Noctuidae) in Laboratory and Field Studies," J. Econ. Entomol. 90(3)723–731 (1997), Kanga et al., "Tolerance to Cypermethrin and Endosulfan in Field Populations of the Bollworm (Lepidoptera: Noctuidae) from Texas," J. Econ. Entomol. 89(3)583–589 (1996), Kanga et al., "Monitoring for Resistance to Organophosphorus, Carbamate, and Cyclodiene Insecticides in Tobacco Budworm Adults (Lepidopteria: Noctuidae)," J. Econ. Entomol. 88(5) 1144–1149 (1995), and Elzen et al., "Resistance to Pyrethroids, Carbamate, and Organophosphate Insecticides in Field Populations of Tobacco Budworms (Lepidoptera: Noctuidae) in 1990," J. Econ. Entomol. 85(6):2064–2072 (1992).

New and better control alternatives are always needed to maintain crop production and provide alternative chemistry for rotation purposes, as discussed in Laws, Delta Agricultural Digest, Intertec Publishing (1998).

While the compositions in the art have provided some control of Lepidopteran pests of cotton, there has been a need in the art for significantly greater control.

SUMMARY OF THE INVENTION

An object of the present invention is to provide significantly greater control of tobacco budworm, cotton bollworm, and other Lepidopteran pests of cotton than has been provided previously in the art.

Accordingly, the present inventors conducted extensive experimentation and, as a result, they achieved the present invention, which provides a novel and highly effective, multi-chemistry alternative that provides synergistic results for the control of Lepidopteran insects on cotton and other crops on which they might be present.

In particular, the present invention is directed to an insecticidal composition comprising (1) at least one compound of formula (I):

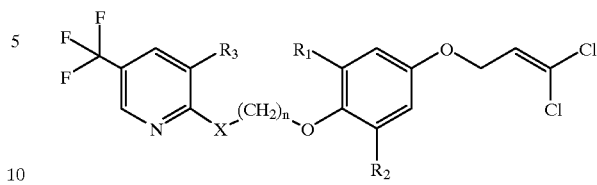

(I)

wherein $R_1$ is bromine, chlorine, methyl, or ethyl, $R_2$ is bromine, chlorine, or ethyl, $R_3$ is hydrogen, halogen, or trifluoromethyl, X is —O—, —S—, or —NH—, and n is 2, 3, or 4, and (2) at least one compound of formula (II):

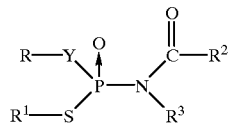

(II)

wherein R and $R^1$ independently are an alkyl, alkenyl, or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms, or an alkynyl group containing 3 to 18 carbon atoms, $R^3$ is hydrogen or an alkyl group containing 1 to 6 carbon atoms, and Y is —O— or —S—.

Also, the present invention is directed to a method of killing Lepidopteran insects comprising applying to an area to be treated an insecticidally effective amount of a composition comprising (1) at least one compound of formula (I):

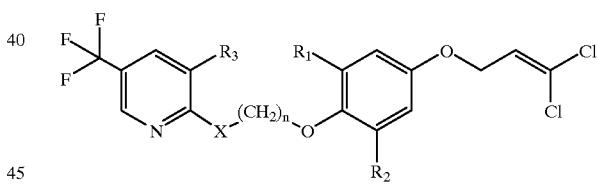

(I)

wherein $R_1$ is bromine, chlorine, methyl, or ethyl, $R_2$ is bromine, chlorine, or ethyl, $R_3$ is hydrogen, halogen, or trifluoromethyl, X is —O—, —S—, or —NH—, and n is 2, 3, or 4, and (2) at least one compound of formula (II):

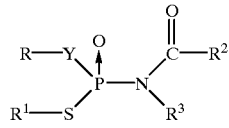

(II)

wherein R and $R^1$ independently are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms, or an alkynyl group containing 3 to 18 carbon atoms, $R^3$ is hydrogen or an alkyl group containing 1 to 6 carbon atoms, and Y is —O— or —S—.

DETAILED DESCRIPTION OF THE INVENTION

One component of the composition of the present invention is a compound of formula (I):

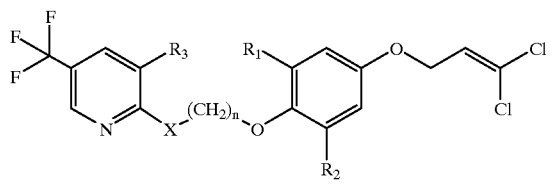

(I)

where $R_1$ is bromine, chlorine, methyl, or ethyl, $R_2$ is bromine, chlorine, 15 or ethyl, $R_3$ is hydrogen, halogen, or trifluoromethyl, X is —O—, —S—, or —NH—, and n is 2, 3, or 4. This compound and methods for its preparation are described in detail in WO 96/11909, which is incorporated herein by reference.

A particularly preferred compound within formula (I) is one in which $R_1$ is chlorine, $R_2$ is chlorine, $R_3$ is hydrogen, X is —O—, and n is 3, i.e., 2-[3-[2,6-dichloro-4-(3,3-dichloroprop-2-enyloxy)phenoxy]propoxy]-5-(trifluoromethyl)pyridine (which has been revised from 3,5-dichloro-4-(3-(5-trifluoromethyl-2-pyridyloxy)propyloxy)-1-(3,3-dichloro-2-propenyloxy)benzene).

A compound of formula (I) can be prepared by the following method.

A compound of formula (a)

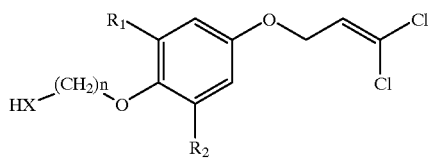

(a)

wherein $R_1$ is bromine, chlorine, methyl, or ethyl, $R_2$ is bromine, chlorine, or ethyl, X is —O—, —S—, or —NH—, and n is 2, 3, or 4, is reacted with a compound of formula (b)

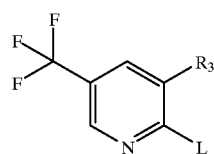

(b)

where $R_3$ is hydrogen, halogen, or trifluoromethyl and L is halogen (e.g., chlorine, bromine, or iodine), mesyloxy, or tosyloxy.

The reaction is preferably effected in an inert solvent in the presence of a suitable base.

Examples of the solvent which can be used are ketones such as acetone, methyl ethyl ketone and cyclohexanone; ethers such as 1,2-dimethoxyethane, tetrahydrofuran, dioxane and dialkyl (e.g., $C_1$–$C_4$) ethers (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used are hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$) such as sodium methoxide, sodium ethoxide and potassium tert-butoxide; and organic bases such as triethylamine and pyridine. If necessary, catalysts such as ammonium salts (e.g., triethylbenzylammonium chloride) may be added to the reaction system at a ratio of 0.01 to 1 mole per mole of the compound of formula (a).

The reaction temperature is usually set within the range of −20° C. to 150° C. or the boiling point of a solvent used in the reaction, preferably −5° C. to 100° C. or the boiling point of a solvent used in the reaction.

The molar ratio of the starting materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallation.

Another component of the composition of the present invention s a compound of formula (II):

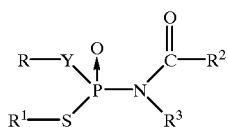

(II)

wherein R and $R^1$ independently are an alkyl, alkenyl, or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms, or an alkynyl group containing 3 to 18 carbon atoms, $R^3$ is hydrogen or an alkyl group containing 1 to 6 carbon atoms, and Y is —O— or —S—. This compound and methods for its preparation are described in detail in U.S. Pat. Nos. 3,176,600, 3,845,172, and 3,914,417, which are incorporated herein by reference.

A preferred compound within formula (II) is one in which R and $R^1$ independently are a methyl, ethyl, allyl or alkenyl group, $R^2$ is hydrogen or an alkyl group, $R^3$ is hydrogen, and Y is —O—.

A particularly preferred compound within formula (II) is one in which R, $R^1$ and $R^2$ are methyl groups, $R^3$ is hydrogen, and Y is —O—. This compound is known as acephate and is commercially available, e.g., from the Chevron Chemical Company under the trade name Orthene®.

The composition of the present invention comprises a mixture of at least one compound of formula (I) and at least one compound of formula (II). A particularly preferred composition of the present invention comprises a mixture of 2-[3-[2,6-dichloro-4-(3,3-dichloroprop-2-enyloxy)phenoxy]propoxy]-5-(trifluoromethyl)pyridine (hereinafter referred to as "S-1812" for convenience) and acephate.

In the composition of the present invention, the ratio of the compound of formula (I): the compound of formula (II) can vary preferably from 1:3.3 to 1:127.8, more preferably from 1:3.3 to 1:64, even more preferably from 1:3.3 to 1:15, on a parts by weight basis. For example, the ratio of S-1812:acephate can vary from I part S-1812:5 parts acephate to 1 part S-1812:127.8 parts acephate. As an example within this range, the ratio of S-1812:acephate can vary from 1 part S-1812:16 parts acephate to 1 part S-1812:127.8 parts acephate. As another example within this range, the ratio of S-1812:acephate can vary from 1 part S-1812:5 parts acephate to 1 part S-1 812:10 parts acephate.

Other components which can be present in the invention composition include emulsifiers and solvents. For example, an emulsifiable concentrate formulation of S-1812 can be prepared using anionic-nonionic emulsifier blends such as Atlox 3454 and Atlox 3455, manufactured by Uniqema (formerly ICI Surfactants), and an aromatic hydrocarbon solvent such as Solvesso 150, manufactured by Exxon Chemical Company. When added to water, this formulation of S-1 812 forms a solution containing S-1812 which can then be added to an acephate-containing solution to form a solution of the composition of the present invention.

Once formulated, the invention composition is useful in a method for controlling Lepidopteran insects by application of the composition onto the insecticidal habitat. In general, the invention composition can be applied onto the habitat in an amount effective to be insecticidal to the insects.

In the solution application of the present invention, the invention composition can be dissolved in from about 3 gallons to about 10 gallons of water for application per acre, such that preferably at least about 0.063 lb and 0.5 lb of active ingredient (compounds of formula (I) and formula (II), respectively), more preferably from about 0.063 lb and 0.5 lb to about 0.1 lb and 0.75 lb of active ingredient is applied per acre.

The composition of the present invention has been demonstrated in the laboratory and in the field to be highly effective against Lepidopteran insects, bollworm, beet armyworm, soybean looper, and tarnished plant bug, providing synergistic results as compared with the performance of the individual active ingredients. As a result, the present invention provides excellent control of Lepidopteran pests of cotton and other crops on which they might occur.

The following examples illustrate specific embodiments of the present invention, but should not be construed as limiting the scope of the claims in any way. All parts, percents, ratios and the like are by weight unless otherwise indicated.

EXAMPLES

Example 1

An S-1812-containing formulation identified as "S-1812 0.83EC" was prepared by mixing the following components (w/v%):

| | |
|---|---|
| S-1812 (active ingredient) | 10.3% |
| Atlox 3454F (emulsifier) | 2.0% |
| Atlox 3455F (emulsifier) | 8.0% |
| Solvesso 150 (solvent) | 79.7% |
| Total | 100.0% |

As set forth above, S-1812 0.83EC has 10.3% ai on a w/v% basis, i.e., 0.83 lb ai/gallon [(0.1 g ai/ml)(3785 ml/1 gallon)(1 lb/454 g)].

0.2 g of S-1812 0.83EC was added to 800 ml distilled $H_2O$ and stirred to give a 25 ppmai (parts per million active ingredient) solution. This solution was serially diluted by 300 ml stock/300 ml distilled $H_2O$ to yield solution concentrations of 12.5, 6.25 and 3.13 ppmai.

0.02 g of acephate (Orthene, technical grade, 98% pure) was added to 50 ml of S-1812 6.25 ppmai stock and 50 ml of S-1812 3.13 ppmai stock to give 400 ppmai acephate +6.25 ppmai S-1812, and 400 ppmai acephate +3.13 ppmai S-1 812 mixtures.

The above procedure was repeated with 0.01g of acephate to yield 200 ppmai acephate+6.25 or 3.13 ppmai S-1812 mixtures.

The procedure set forth in the preceding paragraph was repeated with 100 ml of S-1812 3.13 or 6.25 ppmai stock to yield 100 ppmai acephate+6.25 or 3.13 ppmai S-1812 mixtures.

Solutions of acephate alone of the various concentrations were prepared in a similar manner using distilled $H_2O$.

The testing substrate was composed of 2.0 ml of prepared artificial tobacco budworm diet mix (Bio-Serv) dispensed into the bottom of a clear one ounce cup. The diet was dispensed in such a way that the surface when dry was level and smooth (no pits).

0.2 ml of the test mixture was pipetted onto the surface of the diet. The treated diet was placed under a fume hood to dry the test solution onto the diet surface (approximately one hour).

After drying, one second instar tobacco budworm larvae was placed into each cup, and the cup was seated with a tight fitting, but not airtight, lid. The cups were held at 25° C. and 50% RH and evaluated after seven days. Larvae were rated as dead or alive at this point. There were 20 replicates per treatment with one cup=one replication.

The results of this testing are shown in Table 1 below.

TABLE 1

SYNERGISM BETWEEN ORTHENE AND S-1812
IN A LABORATORY EXPERIMENT WITH SECOND
INSTAR TOBACCO BUDWORM LARVAE

| S-1812 Ppm ai | S-1812 % Mortality | Orthene Ppm ai | Orthene % Mortality | S-1812 & Orthene Additive % Mortality | S-1812 Ppm ai + Orthene Ppm ai (Mixture) | Mixture % Mortality | Increase In % Mortality of Mixture Over Additive |
|---|---|---|---|---|---|---|---|
| 3.13 | 5 | 100 | 10 | 15 | 3.13 + 100 | 35 | 20 |
| 3.13 | 5 | 200 | 5 | 10 | 3.13 + 200 | 25 | 15 |
| 3.13 | 5 | 400 | 30 | 35 | 3.13 + 400 | 75 | 40 |
| 6.25 | 30 | 100 | 10 | 40 | 6.25 + 100 | 65 | 25 |
| 6.25 | 30 | 200 | 5 | 35 | 6.25 + 200 | 65 | 30 |
| 6.25 | 30 | 400 | 30 | 60 | 6.25 + 400 | 100 | 40 |

As can be seen from the results presented above in Table 1, the compounds of formulas (I) and (II) act synergistically together to increase the mortality rate beyond the sum of the rates for the compounds individually and thereby provide unexpectedly superior control of a Lepidopteran pest.

Example 2

Spray treatments were applied by a tractor mounted (highboy) spray boom to cotton field plots in Greenville, Mississippi that measured 40–50 ft by 13.2 ft by 13.2 ft with 3–4 replications per treatment. Treatments were applied at 10 gallons of spray volume per acre. Tank-mixes were made by measuring both compounds independently and then adding them to the appropriate amount of water to produce the spray mixture. Treatments were applied in July/August at approximately one week intervals.

Plots were evaluated by sampling all damaged and undamaged bolls on 10 plants per plot. Cotton plots were evaluated for yield by machine picking the center two rows of each plot. The results are shown in Table 2 below.

TABLE 2

FIELD EFFICACY OF S-1812 + ORTHENE AGAINST
TOBACCO BUDWORM AND COTTON BOLLWORM IN COTTON

| Trt | Application | No. of Applications | Product | Conc/FM | Lb al/A Application Rate | Meth | % Damaged Bolls | Bolls/ Plant | Yield-Lbs Seed Cotton/A |
|---|---|---|---|---|---|---|---|---|---|
| 1 | | 0 | UTC | | | | 55.30 | 3.87 | 843.55 |
| 2 | ABCDE | 5 | Curacron | 8EC | .500 | FOSP | 26.33 | 8.70 | 1578.26 |
| 3 | ABCDE | | Larvin | 3.2FL | .300 | FOSP | | | |
| 3 | ABCDE | 5 | AsanaXL | .66EC | .050 | FOSP | 16.63 | 7.30 | 1823.16 |
| 4 | ABCDE | 5 | Karate | 1.0EC | .040 | FOSP | 23.27 | 8.00 | 1687.10 |
| 5 | AC | 2 | AsanaXL | .66EC | .050 | FOSP | 38.90 | 5.63 | 1142.88 |
| 6 | ABCDE | 5 | Orthene | 90SP | 1.0 | FOSP | 21.40 | 7.10 | 1537.45 |
| 7 | ABCDE | 5 | S-1812 | .83EC | .150 | FOSP | 14.37 | 7.93 | 1972.82 |
| 8 | AC | 2 | S-1812 | .83EC | .150 | FOSP | 23.53 | 7.07 | 1551.05 |
| 9 | ABCDE | 5 | S-1812 | .83EC | .075 | FOSP | 14.10 | 8.83 | 2204.12 |
| | ABCDE | | Orthene | 90SP | .500 | FOSP | | | |
| | | | CV | | | | 34.34 | 23.20 | 15.04 |
| | | | LSD | | | | 16.78 | 2.69 | 388.02 |

Trt = treatment
Conc/FM = concentration and formulation
FOSP = foliar spray method
ABCDE (under Application) = five applications, coded A, B, C, D & E
UTC = untreated cotton
Curacron = profenofos
Larvin = thiodicarb
AsanaXL = esfenvalerate
Karate = lambda cyhalothrin
Orthene = acephate
EC = emulsifiable concentrate
FL = flowable concentrate
SP = soluble powder
8EC has 8 lb ai/gallon
3.2FL has 3.2 lb ai/gallon
.66EC has 0.66 lb ai/gallon
1.0EC has 1.0 lb ai/gallon
90SP has 90% ai on a per weight basis
.83EC has 0.83 lb ai/gallon
CV = Coefficient of Variation (a statistic for comparison of like experiments)
LSD = Fisher's Least Significant Difference (a statistical method of comparing two means for significant difference by providing the smallest valid difference)

As can be seen from the data presented above in Table 2, a mixture of compounds of formulas (I) and (II) provides unexpectedly superior results with respect to reducing the percentage of damaged bolls, providing a higher number of bolls per plant, and providing a higher yield in pounds of seed cotton per acre as compared with the use of compounds of formulas (I) and (II) individually and as compared with the use of other insecticides.

Example 3

Additional testing was conducted against a variety of Lepidopteran pests as shown in Table 3 below.

TABLE 3

Test Subjects

| Crop | | | | | | | GOSHJ | SPOEI | TRINI | GOSHJ | SPOEI | TRINI | LYLGI |
|---|---|---|---|---|---|---|---|---|---|---|---|---|---|
| Pest | | | | | | | | | | | | | |
| Test Subject No. | | | | | | | 1 | 2 | 3 | 1 | 2 | 3 | 4 |
| Reporting Standard | | | | | | | PDSQ | NOTF | NOTF | PDSQ | NOTF | NOTF | NOSW |
| Comment | | | | | | | | | | | | | ADULT |
| Days After Trt | | | | | | | 6 DA-A | 6 DA-A | 6 DA-A | 2 DA-C | 2 DA-C | 2 DA-C | 3 DA-C |
| Trt No | Product | Form Conc | Fm Tp | Appl Rate | Rate Unit | Appl Meth | Appl Code | | | | | | |
| 1 | UTC | | | | | | | 31.0 a | 54.0 a | 11.8 a | 35.0 a | 16.5 a | 6.8 a | 0.120 a |
| 2 | S1812 | 35 | WP | .05 | LBAI/A | FOSP | ABCDE | 21.0 ab | 7.8 c | 6.8 a | 7.0 de | 3.3 cd | 2.5 de | 0.030 ab |
| 2 | ORTHENE | 90 | SP | .75 | LBAI/A | FOSP | ABCDE | | | | | | | |
| 3 | S1812 | 35 | WP | .063 | LBAI/A | FOSP | ABCDE | 14.0 b | 17.8 bc | 8.0 a | 10.0 cde | 1.5 d | 2.3 de | 0.050 ab |
| 3 | ORTHENE | 90 | SP | .5 | LBAI/A | FOSP | ABCDE | | | | | | | |
| 4 | S1812 | 35 | WP | .063 | LBAI/A | FOSP | ABCDE | 16.0 b | 9.5 bc | 9.5 a | 6.0 de | 4.3 cd | 1.3 e | 0.000 b |
| 4 | ORTHENE | 90 | SP | .75 | LBAI/A | FOSP | ABCDE | | | | | | | |
| 5 | S1812 | 35 | WP | .075 | LBAI/A | FOSP | ABCDE | 16.0 b | 12.5 bc | 11.3 a | 6.0 de | 6.3 cd | 2.8 de | 0.030 ab |
| 5 | ORTHENE | 90 | SP | .5 | LBAI/A | FOSP | ABCDE | | | | | | | |
| 6 | S1812 | 35 | WP | .1 | LBAI/A | FOSP | ABCDE | 13.0 b | 13.3 bc | 10.5 a | 6.0 de | 3.0 cd | 2.3 de | 0.030 ab |
| 6 | ORTHENE | 90 | SP | .33 | LBAI/A | FOSP | ABCDE | | | | | | | |
| 7 | ORTHENE | 90 | SP | .33 | LBAI/A | FOSP | ABCDE | 19.0 ab | 14.5 bc | 13.0 a | 17.0 bcd | 14.8 ab | 5.8 abc | 0.110 a |
| 8 | ORTHENE | 90 | SP | .5 | LBAI/A | FOSP | ABCDE | 11.0 b | 54.5 a | 11.8 a | 12.0 b–e | 10.5 abc | 3.5 b–e | 0.050 ab |
| 9 | ORTHENE | 90 | SP | .75 | LBAI/A | FOSP | ABCDE | 20.0 ab | 24.0 abc | 9.5 a | 21.0 bc | 8.5 bcd | 3.8 b–e | 0.060 ab |
| 10 | S1812 | 35 | WP | .05 | LBAI/A | FOSP | ABCDE | 16.0 b | 25.8 abc | 7.0 a | 7.0 de | 6.0 cd | 5.0 a–d | 0.080 ab |
| 11 | S1812 | 35 | WP | .063 | LBAI/A | FOSP | ABCDE | 14.0 b | 20.3 bc | 11.0 a | 23.0 b | 6.8 cd | 6.3 ab | 0.060 ab |
| 12 | S1812 | 35 | WP | .075 | LBAI/A | FOSP | ABCDE | 22.0 ab | 43.0 ab | 10.0 a | 13.0 b–e | 7.0 cd | 3.3 cde | 0.120 a |
| 13 | S1812 | 35 | WP | .1 | LBAI/A | FOSP | ABCDE | 19.0 ab | 14.8 bc | 10.0 a | 17.0 bcd | 3.5 cd | 1.3 e | 0.070 ab |
| 14 | TRACER | 4 | SC | .09 | LBAI/A | FOSP | ABCDE | 10.0 b | 9.8 bc | 3.8 a | 3.0 e | 2.8 cd | 1.3 e | 0.040 ab |
| LSD (P = .05) | | | | | | | | 12.60 | 29.53 | 7.89 | 10.11 | 7.13 | 2.63 | 0.0891 |
| Standard Deviation | | | | | | | | 8.82 | 20.67 | 5.52 | 7.07 | 4.99 | 1.84 | 0.0624 |
| CV | | | | | | | | 51.02 | 90.07 | 57.79 | 54.12 | 73.93 | 53.89 | 102.7 |
| Replicate F | | | | | | | | 0.064 | 0.821 | 1.924 | 1.574 | 1.638 | 8.138 | 0.341 |
| Replicate Prob (F) | | | | | | | | 0.9787 | 0.4904 | 0.1417 | 0.2111 | 0.1963 | 0.0002 | 0.7961 |
| Treatment F | | | | | | | | 1.483 | 2.401 | 0.790 | 6.203 | 3.259 | 4.128 | 1.353 |
| Treatment Prob (F) | | | | | | | | 0.1677 | 0.0174 | 0.6658 | 0.0001 | 0.0021 | 0.0003 | 0.2261 |

Means followed by same letter do not significantly differ (P = .05, Duncan's New MRT)

Test Subjects

| Crop | | | | | | | | | | | | GOSHJ | |
|---|---|---|---|---|---|---|---|---|---|---|---|---|---|
| Pest | | | | | | | COCCI | GEOPU | CHRCA | ARACH | LYLGI | | SPOEI |
| Test Subject No. | | | | | | | 5 | 6 | 7 | 8 | 9 | 1 | 2 |
| Reporting Standard | | | | | | | NOSW | NOSW | NOSW | NOSW | NOSW | PDSQ | NOTF |
| Comment | | | | | | | | | | | NYMPH | | |
| Days After Trt | | | | | | | 3 DA-C | 3 DA-C | 3 DA-C | 3 DA-C | 3 DA-C | 2 DA-D | 2 DA-D |
| Trt No | Product | Form Conc | Fm Tp | Appl Rate | Rate Unit | Appl Meth | Appl Code | | | | | | |
| 1 | UTC | | | | | | | 0.230 abc | 0.020 b | 0.030 a | 0.000 b | 0.100 abc | 49.0 a | 25.3 bc |
| 2 | S1812 | 35 | WP | .05 | LBAI/A | FOSP | ABCDE | 0.240 abc | 0.000 b | 0.010 a | 0.000 b | 0.010 d | 7.0 cd | 13.3 bc |
| 2 | ORTHENE | 90 | SP | .75 | LBAI/A | FOSP | ABCDE | | | | | | | |
| 3 | S1812 | 35 | WP | .063 | LBAI/A | FOSP | ABCDE | 0.240 abc | 0.000 b | 0.010 a | 0.000 b | 0.030 cd | 14.0 cd | 6.8 c |
| 3 | ORTHENE | 90 | SP | .5 | LBAI/A | FOSP | ABCDE | | | | | | | |
| 4 | S1812 | 35 | WP | .063 | LBAI/A | FOSP | ABCDE | 0.120 c | 0.010 b | 0.000 a | 0.010 a | 0.000 d | 10.0 cd | 15.3 bc |
| 4 | ORTHENE | 90 | SP | .75 | LBAI/A | FOSP | ABCDE | | | | | | | |
| 5 | S1812 | 35 | WP | .075 | LBAI/A | FOSP | ABCDE | 0.290 abc | 0.000 b | 0.010 a | 0.000 b | 0.000 d | 9.0 cd | 25.8 bc |
| 5 | ORTHENE | 90 | SP | .5 | LBAI/A | FOSP | ABCDE | | | | | | | |
| 6 | S1812 | 35 | WP | .1 | LBAI/A | FOSP | ABCDE | 0.170 bc | 0.010 b | 0.010 a | 0.000 b | 0.020 cd | 12.0 cd | 13.5 bc |
| 6 | ORTHENE | 90 | SP | .33 | LBAI/A | FOSP | ABCDE | | | | | | | |
| 7 | ORTHENE | 90 | SP | .33 | LBAI/A | FOSP | ABCDE | 0.220 abc | 0.020 b | 0.010 a | 0.000 b | 0.050 bcd | 29.0 b | 79.3 a |
| 8 | ORTHENE | 90 | SP | .5 | LBAI/A | FOSP | ABCDE | 0.330 ab | 0.000 b | 0.000 a | 0.000 b | 0.020 cd | 14.0 cd | 68.8 a |
| 9 | ORTHENE | 90 | SP | .75 | LBAI/A | FOSP | ABCDE | 0.260 abc | 0.000 b | 0.000 a | 0.000 b | 0.000 d | 20.0 bc | 45.5 ab |
| 10 | S1812 | 35 | WP | .05 | LBAI/A | FOSP | ABCDE | 0.330 ab | 0.000 b | 0.020 a | 0.000 b | 0.100 abc | 9.0 cd | 10.5 bc |
| 11 | S1812 | 35 | WP | .063 | LBAI/A | FOSP | ABCDE | 0.300 abc | 0.050 a | 0.010 a | 0.000 b | 0.040 cd | 8.0 cd | 14.0 bc |
| 12 | S1812 | 35 | WP | .075 | LBAI/A | FOSP | ABCDE | 0.350 ab | 0.000 b | 0.020 a | 0.000 b | 0.130 ab | 17.0 bcd | 8.8 bc |
| 13 | S1812 | 35 | WP | .1 | LBAI/A | FOSP | ABCDE | 0.290 abc | 0.000 b | 0.020 a | 0.000 b | 0.100 abc | 14.0 cd | 3.5 c |

TABLE 3-continued

| Trt | Product | Form Conc | Fm Tp | Appl Rate | Rate Unit | Appl Meth | Appl Code | | | | | | | |
|---|---|---|---|---|---|---|---|---|---|---|---|---|---|---|
| 14 | TRACER | 4 | SC | .09 | LBAI/A | FOSP | ABCDE | 0.390 a | 0.010 b | 0.010 a | 0.000 b | 0.140 a | 2.0 d | 3.5 c |
| LSD (P = .05) | | | | | | | | 0.1702 | 0.0272 | 0.0341 | 0.0077 | 0.0746 | 12.87 | 32.87 |
| Standard Deviation | | | | | | | | 0.1191 | 0.0191 | 0.0238 | 0.0054 | 0.0522 | 9.00 | 23.00 |
| CV | | | | | | | | 44.34 | 222.39 | 208.63 | 758.11 | 98.71 | 58.9 | 96.56 |
| Replicate F | | | | | | | | 5.614 | 0.210 | 1.072 | 0.974 | 0.518 | 0.390 | 1.753 |
| Replicate Prob (F) | | | | | | | | 0.0027 | 0.8891 | 0.3721 | 0.4149 | 0.6725 | 0.7608 | 0.1721 |
| Treatment F | | | | | | | | 1.479 | 2.177 | 0.526 | 0.974 | 3.762 | 6.722 | 4.348 |
| Treatment Prob (F) | | | | | | | | 0.1693 | 0.0306 | 0.8943 | 0.4927 | 0.0007 | 0.0001 | 0.0002 |

Means followed by same letter do not significantly differ (P = .05, Duncan's New MRT)

Test Subjects

| | | | | | | | | | GOSHJ | GOSHJ |
|---|---|---|---|---|---|---|---|---|---|---|
| Crop | | | | | | | | | | |
| Pest | | | | | | | | TRINI | | |
| Test Subject No. | | | | | | | | 3 | 10 | 11 |
| Reporting Standard | | | | | | | | NOTF | NOBP | PDBO |
| Comment | | | | | | | | | | |
| Days After Trt | | | | | | | | 2 DA-D | | |

| Trt No | Product | Form Conc | Fm Tp | Appl Rate | Rate Unit | Appl Meth | Appl Code | | | |
|---|---|---|---|---|---|---|---|---|---|---|
| 1 | UTC | | | | | | | 6.0 ab | 29.8 d | 37.65 a |
| 2 | S1812 | 35 | WP | .05 | LBAI/A | FOSP | ABCDE | 3.3 bc | 61.0 bc | 12.65 cd |
| 2 | ORTHENE | 90 | SP | .75 | LBAI/A | FOSP | ABCDE | | | |
| 3 | S1812 | 35 | WP | .063 | LBAI/A | FOSP | ABCDE | 1.5 c | 69.3 abc | 11.82 cd |
| 3 | ORTHENE | 90 | SP | .5 | LBAI/A | FOSP | ABCDE | | | |
| 4 | S1812 | 35 | WP | .063 | LBAI/A | FOSP | ABCDE | 2.8 bc | 84.3 ab | 11.45 cd |
| 4 | ORTHENE | 90 | SP | .75 | LBAI/A | FOSP | ABCDE | | | |
| 5 | S1812 | 35 | WP | .075 | LBAI/A | FOSP | ABCDE | 2.3 bc | 71.3 abc | 14.73 cd |
| 5 | ORTHENE | 90 | SP | .5 | LBAI/A | FOSP | ABCDE | | | |
| 6 | S1812 | 35 | WP | .1 | LBAI/A | FOSP | ABCDE | 3.5 bc | 83.8 ab | 14.48 cd |
| 6 | ORTHENE | 90 | SP | .33 | LBAI/A | FOSP | ABCDE | | | |
| 7 | ORTHENE | 90 | SP | .33 | LBAI/A | FOSP | ABCDE | 8.5 a | 52.0 c | 28.00 ab |
| 8 | ORTHENE | 90 | SP | .5 | LBAI/A | FOSP | ABCDE | 6.0 ab | 54.3 c | 33.40 ab |
| 9 | ORTHENE | 90 | SP | .75 | LBAI/A | FOSP | ABCDE | 5.3 abc | 57.5 c | 22.03 bc |
| 10 | S1812 | 35 | WP | .05 | LBAI/A | FOSP | ABCDE | 6.3 ab | 75.3 abc | 10.58 cd |
| 11 | S1812 | 35 | WP | .063 | LBAI/A | FOSP | ABCDE | 4.5 abc | 60.5 bc | 9.02 cd |
| 12 | S1812 | 35 | WP | .075 | LBAI/A | FOSP | ABCDE | 3.0 bc | 56.5 c | 13.83 cd |
| 13 | S1812 | 35 | WP | .1 | LBAI/A | FOSP | ABCDE | 3.5 bc | 67.8 abc | 7.30 d |
| 14 | TRACER | 4 | SC | .09 | LBAI/A | FOSP | ABCDE | 2.8 bc | 87.5 a | 2.55 d |
| LSD (P = .05) | | | | | | | | 3.65 | 21.58 | 11.261 |
| Standard Deviation | | | | | | | | 2.56 | 15.10 | 7.880 |
| CV | | | | | | | | 60.65 | 23.22 | 48.07 |
| Replicate F | | | | | | | | 5.853 | 6.190 | 0.961 |
| Replicate Prob (F) | | | | | | | | 0.0021 | 0.0015 | 0.4208 |
| Treatment F | | | | | | | | 2.307 | 4.171 | 6.652 |
| Treatment Prob (F) | | | | | | | | 0.0221 | 0.0003 | 0.0001 |

Means followed by same letter do not significantly differ (P = .05, Duncan's New MRT)

Trt = treatment
UTC = untreated cotton
WP = wettable powder
SP = soluble powder
SC = soluble concentrate
35 WP has 35% ai on a per weight basis
90 SP has 90% ai on a per weight basis
4 SC has 4 lb ai/gallon
FOSP = foliar spray method
GOSHJ = cotton
SPOEI = beet armyworm, *Spodoptera exigua*
TRINI = cabbage looper, *Trichoplusia ni*
LYGLI = Tarnished plant bug, *Lygus lineolaris*
COCCI = ladybird beetles
GEOPU = bigeyed bug
CHRCA = lacewings
ARACH = spider
PDSQ = percent damaged cotton squares
NOTF = number per 10 row feet using beat cloth sampling method
NOSW = number per swing of a sweep net
NOBP = number of cotton bolls (fruits) per cotton plant
PDBO = percent damaged cotton bolls
6 DA-A = 6 days after application A
Tracer = Spinosyn A + Spinosyn D
CV = Coefficient of Variation
LSD = Fisher's Least Significant Difference
A treatment is a particular insecticide or insecticide mixture being tested.
The number of replicates or replications is the number of times a treatment is identically repeated within the same test (for example, tested on 3–4 plots in a field test).

As can be seen from the results presented above in Table 3, the mixture of compounds as in the present invention again provided unexpectedly superior results as compared with the compounds individually and as compared with another insecticidal mixture.

While the invention has been described in detail and with reference to specific embodiments thereof, it will be apparent to one skilled in the art that various changes and modifications can be made therein without departing from the spirit and scope thereof.

What is claimed is:

1. An insecticidal composition comprising synergistically in secticidally effective amounts of (1) at least one compound of formula (I):

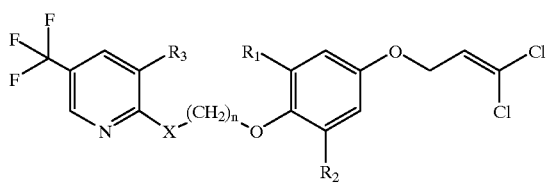

(I)

wherein $R_1$ is bromine, chlorine, methyl, or ethyl, $R_2$ is bromine, chlorine, or ethyl, $R_3$ is hydrogen, halogen or trifluoromethyl, X is —O—, —S—, or —NH—, and n is 2, 3, or 4, and (2) at least one compound of formula (II):

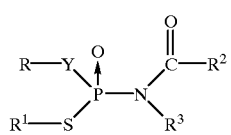

(II)

wherein R and $R^1$ independently are an alkyl, alkenyl, or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms, or an alkynyl group containing 3 to 18 carbon atoms, $R^3$ is hydrogen or an alkyl group containing 1 to 6 carbon atoms, and Y is —O— or —S—.

2. An insecticidal composition as in claim 1, wherein the at least one compound of formula (I) is 2-[3-[2,6-dichloro-4-(3,3-dichloroprop-2-enyloxy)phenoxy]propoxy]-5-(trifluoromethyl )pyridine.

3. An insecticidal composition as in claim 1, wherein the at least one compound of formula (II) is a compound in which R and $R^1$ independently are a methyl, ethyl, allyl or alkenyl group, $R^2$ is hydrogen or an alkyl group, $R^3$ is hydrogen, and Y is —O—.

4. An insecticidal composition as in claim 3, wherein the at least one compound of formula (II) is acephate.

5. An insecticidal composition as in claim 2, wherein the at least one compound of formula (II) is a compound in which R and $R^1$ independently are a methyl, ethyl, allyl or alkenyl group, $R^2$ is hydrogen or an alkyl group, $R^3$ is hydrogen, and Y is —O—.

6. An insecticidal composition as in claim 5, wherein the at least one compound of formula (II) is acephate.

7. An insecticidal composition as in claim 6, wherein (A) the 2-[3-[2,6-dichloro-4-(3,3-dichloroprop-2-enyloxy) phenoxy]propoxy]-5-(trifluoromethyl)pyridine and (B) the acephate are present in an (A):(B) ratio of 1:5 to 1:127.8 on a parts by weight basis.

8. An insecticidal composition as in claim 7, wherein (A) the 2-[3-[2,6-dichloro-4-(3,3-dichloroprop-2-enyloxy) phenoxy]propoxy]-5-(trifluoromethyl)pyridine and (B) the acephate are present in an (A):(B) ratio of 1:16 to 1:127.8 on a parts by weight basis.

9. An insecticidal composition as in claim 7, wherein (A) the 2-[3-[2,6-dichloro-4-(3,3-dichloroprop-2-enyloxy) phenoxy]propoxy]-5-(trifluoromethyl)pyridine and (B) the acephate are present in an (A):(B) ratio of 1:5 to 1:10 on a parts by weight basis.

10. A method for killing Lepidopteran insects, comprising applying to an area to be treated synergistically insecticidally effective amounts of a composition comprising (1) at least one compound of formula (I):

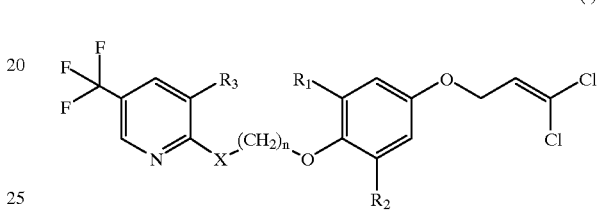

(I)

wherein $R_1$ is bromine, chlorine, methyl, or ethyl, $R_2$ is bromine, chlorine, or ethyl, $R_3$ is hydrogen, halogen or trifluoromethyl, X is —O—, —S—, or —NH—, and n is 2, 3, or 4, and (2) at least one compound of formula (II):

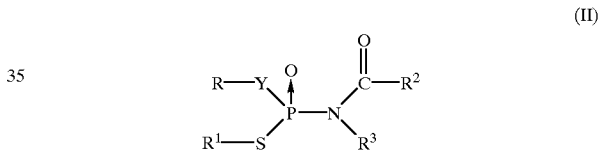

(II)

wherein R and $R^1$ independently are an alkyl, alkenyl, or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms, or an alkynyl group containing 3 to 18 carbon atoms, $R^3$ is hydrogen or an alkyl group containing 1 to 6 carbon atoms, and Y is —O— or —S—.

11. A method as in claim 10, wherein the at least one compound of formula (I) is 2-[3-[2,6-dichloro-4-(3,3-dichloroprop-2-enyloxy)phenoxy]propoxy]-5-(trifluoromethyl)pyridine.

12. A method as in claim 10, wherein the at least one compound of formula (II) is a compound in which R and $R^1$ independently are a methyl, ethyl, allyl or alkenyl group, $R^2$ is hydrogen or an alkyl group, $R^3$ is hydrogen, and Y is —O—.

13. A method as in claim 12, wherein the at least one compound of formula (II) is acephate.

14. A method as in claim 11, wherein the at least one compound of formula (II) is a compound in which R and $R^1$ independently are a methyl, ethyl, allyl or alkenyl group, $R^2$ is hydrogen or an alkyl group, $R^3$ is hydrogen, and Y is —O—.

15. A method as in claim 14, wherein the at least one compound of formula (II) is acephate.

16. A method as in claim 15, wherein (A) the 2-[3-[2,6-dichloro-4-(3,3-dichloroprop-2-enyloxy)phenoxy]

propoxy]-5-(trifluoromethyl)pyridine and (B) the acephate are present in an (A):(B) ratio of 1:5 to 1:127.8 on a parts by weight basis.

17. A method as in claim 16, wherein (A) the 2-[3-[2,6-dichloro-4-(3,3-dichloroprop-2-enyloxy)phenoxy]propoxy]-5-(trifluoromethyl)pyridine and (B) the acephate are present in an (A):(B) ratio of 1:16 to 1:127.8 on a parts by weight basis.

18. A method as in claim 16, wherein (A) the 2-[3-[2,6-dichloro-4-(3,3-dichloroprop-2-enyloxy)phenoxy]propoxy]-5-(trifluoromethyl)pyridine and (B) the acephate are present in an (A):(B) ratio of 1:5 to 1:10 on a parts by weight basis.

* * * * *